US010729891B2

(12) United States Patent
Werneth et al.

(10) Patent No.: US 10,729,891 B2
(45) Date of Patent: Aug. 4, 2020

(54) GAS-ELIMINATION PATIENT ACCESS DEVICE

(71) Applicant: Acutus Medical, Inc., Carlsbad, CA (US)

(72) Inventors: Randell L. Werneth, Eagle, ID (US); David Zarbatany, Laguna Niguel, CA (US); Mark MacGregor, St. Paul, MN (US); Ricardo David Roman, Chula Vista, CA (US); R. Maxwell Flaherty, Topsfield, MA (US); J. Christopher Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 0 days.

(21) Appl. No.: 16/111,538

(22) Filed: Aug. 24, 2018

(65) Prior Publication Data
US 2019/0054276 A1    Feb. 21, 2019

Related U.S. Application Data

(63) Continuation of application No. 15/111,690, filed as application No. PCT/US2015/011312 on Jan. 14, 2015, now Pat. No. 10,071,227.
(Continued)

(51) Int. Cl.
*A61M 25/06* (2006.01)
*A61M 5/36* (2006.01)
(Continued)

(52) U.S. Cl.
CPC .......... *A61M 25/0662* (2013.01); *A61M 5/36* (2013.01); *A61M 25/00* (2013.01); *A61M 39/22* (2013.01); *A61M 2205/18* (2013.01)

(58) Field of Classification Search
CPC .............. A61M 1/3626; A61M 1/3627; A61M 2005/1652; A61M 2005/1655;
(Continued)

(56) References Cited

U.S. PATENT DOCUMENTS

| 4,954,129 A | 9/1990 | Giuliani et al. |
|---|---|---|
| 6,878,132 B2 | 4/2005 | Kipfer |

(Continued)

FOREIGN PATENT DOCUMENTS

| JP | 2003511104 | 3/2003 |
|---|---|---|
| JP | 2003207438 | 7/2003 |

(Continued)

OTHER PUBLICATIONS

International Search Report and Written Opinion dated May 11, 2015 in corresponding PCT Application No. PCT/US2015/011312.
(Continued)

*Primary Examiner* — Nathan R Price
*Assistant Examiner* — Melissa A Snyder
(74) *Attorney, Agent, or Firm* — Onello & Mello, LLP

(57) ABSTRACT

Disclosed are devices, systems, and methods for providing access to a patient. The patient access device comprises a proximal end, a distal end and a lumen therethrough. The patient access device further comprises a hollow shaft, an input port and a liquid supply port. At least a portion of the lumen passes through the shaft. The input port is coupled to the lumen, and the lumen and the input port are constructed and arranged to receive an elongate probe. The liquid supply port is in fluid communication with the lumen. The patient access is constructed and arranged to reduce gas from exiting the distal end while a portion of the elongate probe is positioned in the patient access device.

20 Claims, 8 Drawing Sheets

Related U.S. Application Data

(60) Provisional application No. 61/928,704, filed on Jan. 17, 2014.

(51) Int. Cl.
*A61M 25/00* (2006.01)
*A61M 39/22* (2006.01)

(58) Field of Classification Search
CPC .... A61M 25/0662; A61M 5/36; A61M 5/365; A61M 39/22
See application file for complete search history.

(56) References Cited

U.S. PATENT DOCUMENTS

| | | | |
|---|---|---|---|
| 7,615,031 | B2 | 11/2009 | Bonnette et al. |
| 7,935,102 | B2 | 5/2011 | Breznock et al. |
| 8,419,685 | B2 | 4/2013 | Shivkumar et al. |
| 8,431,074 | B2 | 4/2013 | Neer |
| 8,636,692 | B2 | 1/2014 | Roman et al. |
| 8,945,055 | B2 | 2/2015 | Basso et al. |
| 9,320,846 | B2 | 4/2016 | Burns et al. |
| 2002/0107477 | A1 | 8/2002 | Kipfer |
| 2006/0276688 | A1 | 12/2006 | Surti |
| 2007/0060881 | A1 | 3/2007 | Bonnette et al. |
| 2009/0163864 | A1 | 6/2009 | Breznock et al. |
| 2009/0294359 | A1 | 12/2009 | Hopping et al. |
| 2010/0010442 | A1 | 1/2010 | Shivkumar et al. |
| 2011/0125013 | A1 | 5/2011 | Neer |
| 2011/0270182 | A1* | 11/2011 | Breznock ............ A61M 1/3627 604/122 |
| 2012/0197233 | A1 | 8/2012 | Basso et al. |
| 2013/0053693 | A1 | 2/2013 | Breznock et al. |
| 2013/0090607 | A1 | 4/2013 | McKinnon et al. |
| 2013/0123700 | A1 | 5/2013 | Roman et al. |
| 2014/0066891 | A1* | 3/2014 | Burns ................ A61M 5/48 604/506 |
| 2014/0228755 | A1 | 8/2014 | Darrah et al. |

FOREIGN PATENT DOCUMENTS

| | | |
|---|---|---|
| JP | 2011529728 | 12/2011 |
| JP | 2012532716 | 12/2012 |

OTHER PUBLICATIONS

Japanese Office Action dated Dec. 11, 2018 issued in corresponding Japanese Application No. 2016-565100, with machine translation to English.

* cited by examiner

GAS-ELIMINATION PATIENT ACCESS DEVICE

RELATED APPLICATIONS

The present application is a continuation application of U.S. patent application Ser. No. 15/111,690, filed Jul. 14, 2016, now U.S. Pat. No. 10,071,227, which is a 371 national stage application of Patent Cooperation Treaty Application No. PCT/US2015/011312, filed Jan. 14, 2015, which in turn claims priority under 35 USC 119(e) to U.S. Provisional Patent Application Ser. No. 61/928,704, entitled "Gas Elimination Patent Access Device," filed Jan. 17, 2014, which are incorporated herein by reference in their entireties.

FIELD

The present invention is generally related to patient access devices and methods that facilitate the insertion of percutaneous devices into a patient's vascular system or other body lumen, and more particularly, to patient access devices and methods configured to reduce the chance of air or other gas bubbles entering the patient's vascular system during a percutaneous procedure.

BACKGROUND

During many percutaneous procedures, medical devices are inserted into a patient's vascular system and advanced through blood vessels to reach a desired location. Small amounts of air or other gas bubbles can be accidentally introduced into the vascular system during the procedure. For example, gas bubbles can enter the bloodstream as a catheter or other medical device is advanced through a patient access device, such as a vascular introducer sheath, resulting in gas bubbles (i.e. gas emboli) in the bloodstream. Gas bubbles that enter a vein can be captured or otherwise stopped within the lungs. However, if a gas bubble or collection of gas bubbles in the venous system is sufficiently large and becomes trapped in a chamber of the heart, blood flow in the heart can become compromised and can result in serious injury and even death.

One or more gas emboli within an artery, termed arterial gas embolism (AGE), often lead to more serious consequences than gas bubbles in a vein, such as when a gas bubble in an artery stops blood flow to a tissue area fed by the artery. The consequences of 'AGE' depend on the area deprived of blood flow, and can include stroke, if the brain is affected, or a heart attack, if the heart is affected.

Typically, patient access devices, such as vascular introducer sheaths, are used during clinical therapeutic and diagnostic procedures to facilitate insertion and exchange of catheters or other medical devices into a patients' vascular system. The introducer sheaths are tubes inserted into patients' vascular systems to act as guides for the catheters or other medical devices. Once the distal end of the introducer sheath is inserted into a patients' vascular system, the proximal end of the sheath remains outside the patient for the introduction of catheters or other medical devices.

When a catheter or other medical device is inserted into the proximal end of the sheath, air or other gas may be carried into the sheath with the catheter or other medical device, and passed into the patients' vascular system. As discussed above, this gas may form gas emboli when entering the blood stream, preventing normal blood flow to the heart, brain or other body location, and potentially causing tissue damage or even death of the patient. If a first device needs to be replaced with a second device, the first device is withdrawn from the sheath and the second device is then inserted into the sheath, including an additional risk of introducing gas into the patient's vascular system. If the devices used in treating the patient must be exchanged frequently via the sheath, the chance of gas introduction into the patients' vascular system is further increased.

Since typical introducer sheaths and other patient access devices do not prevent introduction of gas into the patient's bloodstream along with the catheter or other medical device being inserted, clinicians are required to manually prevent such an occurrence. Therefore, there is a need for improved patient access devices and methods of device introduction to prevent or reduce the introduction of gas bubbles into the patient's bloodstream to avoid the complications discussed above.

SUMMARY

In accordance with aspects of the present invention, a patient access device comprises a proximal end, a distal end, and a lumen therethrough. The device further comprises a hollow shaft, and at least a portion of the lumen passes through the shaft. The device further comprises an input port coupled to the lumen, and the lumen and the input port are constructed and arranged to receive an elongate probe. The device further comprises a liquid supply port in fluid communication with the lumen, and the patient access device is constructed and arranged to reduce gas from exiting the distal end while a portion of the elongate probe is positioned in the patient access device.

In some embodiments, the patient access device further comprises at least one valve assembly configured to restrict flow between the lumen and an inserted elongate probe. The shaft can comprise a proximal portion and one valve assembly can be positioned on the shaft proximal portion. The shaft can comprise a proximal end and one valve assembly can be attached to the shaft proximal end. The shaft can comprise a distal portion and one valve assembly can be positioned on the shaft distal portion. The one valve assembly can comprise a compressible ring and a compressing collar. The shaft can comprise a thin portion and the valve assembly can be positioned on the shaft thin portion.

In some embodiments, the patient access device further comprises a first valve assembly and a second valve assembly. The first valve assembly can be constructed and arranged to allow flow through the lumen at a first pressure and the second valve assembly can be constructed and arranged to allow flow through the lumen at a second pressure, the second pressure being higher than the first pressure. The first valve assembly can be proximal to the second valve assembly. The patient access device can be constructed and arranged such that when the pressure within the lumen is between the first pressure and the second pressure, fluid passes through the first valve assembly.

In some embodiments, the patient access device is coupled with a patient introducer assembly. The patient introducer assembly can comprise a vascular introducer.

In some embodiments, the patient access device further comprises a conduit. The conduit can be constructed and arranged to be percutaneously inserted into a blood vessel of the patient.

In some embodiments, the patient access device is constructed of one or more biocompatible materials. The biocompatible materials can comprise a material selected from the group consisting of: metal; stainless steel; a cobalt alloy; Ni—Ti alloy; titanium alloy; ceramic; plastic; a polymer;

polyethylene; polyvinylchloride; polyurethane; polylactide; a flexible material; silicone; latex; and/or combinations and/or sub-combinations thereof.

In some embodiments, the shaft comprises a rigid portion and a flexible portion. The patient access device can further comprise a valve assembly surrounding the flexible portion.

In some embodiments, the shaft comprises a transparent portion.

In some embodiments, the input port comprises a valve assembly. The valve assembly can comprise a Tuohy-borst valve assembly.

In some embodiments, the liquid supply port comprises a first fluid port and the patient access device further comprises a second fluid port. The second fluid port can comprise a second liquid supply port. The second fluid port can comprise a fluid output port. The patient access device can further comprise a pump fluidly connected to the liquid supply port and the fluid output port. The shaft can comprise a proximal portion and a distal portion and the liquid supply port can be in fluid communication with the shaft proximal portion and the second fluid port can be in fluid communication with the shaft distal portion.

In some embodiments, the elongate probe comprises a catheter. The elongate probe can comprise an expandable array. The expandable array can comprise a spiral. The expandable array can comprise a basket construction. The expandable array can comprise an array of transducers. The expandable array can comprise an array of sensors. The expandable array can comprise an array of electrodes.

In some embodiments, the liquid supply port is positioned on a proximal portion of the shaft.

In some embodiments, the liquid supply port is positioned on a distal portion of the shaft.

In some embodiments, the liquid supply port comprises a luer.

In some embodiments, the patient access device further comprises a tube fluidly connected to the shaft and the liquid supply port. The tube can comprise a flexible tube. The liquid supply port can comprise a luer fluidly attached to the tube.

In some embodiments, the patient access device further comprises a fluid delivery assembly configured to deliver fluid to the lumen of the shaft. The fluid delivery assembly can be configured to flush fluid over at least a portion of the elongate probe to perform a function selected from the group consisting of one or more of: prevent gas from entering the lumen; drive gas to exit the proximal end of the patient access device; and/or combinations and/or sub-combinations thereof. The fluid delivery assembly can be constructed and arranged to deliver a continuous supply of fluid to the lumen. The fluid delivery assembly can comprise a control configured to allow an operator to initiate the delivery of the fluid. The control can comprise a stopcock. The control can comprise a roller valve. The control can comprise a button configured to be pressed to initiate a flow of fluid. The fluid delivery assembly can comprise a sensor configured to detect insertion of the elongate probe into the input port and the fluid delivery assembly can be configured to automatically deliver fluid based on one or more signals produced by the sensor. The fluid delivery assembly can comprise a gravity-fed source of fluid. The fluid delivery assembly can comprise a pump. The fluid delivery assembly can comprise one or more controls configured to allow an operator to perform a function selected from the group consisting of one or more of: initiate flow of fluid; increase rate of flow of fluid; decrease rate of flow of fluid; set the volume of the flow of fluid; and/or combinations and/or sub-combinations thereof.

In some embodiments, the patient access device further comprises a sensor configured to detect insertion of the elongate probe into a component selected from the group consisting of one or more of: the input port; the lumen; and/or combinations and/or sub-combinations thereof. The patient access device can be configured to automatically initiate the flow of fluid through the lumen based on the detection of the elongate probe by the sensor.

In some embodiments, the patient access device further comprises a flow sensor configured to produce a signal based on fluid flowing through the lumen. The flow sensor can be configured to detect the presence of fluid flow through the lumen. The flow sensor can be configured to detect fluid flow rate through the lumen. The patient access device can be constructed and arranged to maintain a flow rate above 1 ml/min flowing through the lumen. The flow sensor can be configured to produce a signal corresponding to the volume of fluid flowing through the lumen.

In some embodiments, the patient access device further comprises a gas bubble detector. The gas bubble detector can be configured to detect a gas bubble in the lumen. The shaft can comprise a distal portion and the gas bubble detector can be positioned to detect a gas bubble in the shaft distal portion. The gas bubble detector can comprise an ultrasound gas bubble detector.

In some embodiments, the patient access device further comprises a power supply. The power supply can comprise a battery.

In some embodiments, the patient access device further comprises an alarm transducer. The alarm transducer can comprise an audio transducer. The patient access device can be configured to activate the alarm transducer when a condition is detected, the condition selected from the group consisting of one or more of: absence of flow; flow rate below a threshold; presence of a gas bubble; advancement of elongate probe; and/or combinations and/or sub-combinations thereof.

In some embodiments, the patient access device further comprises a gas disrupting component positioned within the lumen. The gas disrupting component can comprise a component selected from the group consisting of one or more of: a wiper; a brush; and/or combinations and/or sub-combinations thereof.

In some embodiments, the patient access device further comprises a second fluid pathway intersecting the lumen. The second fluid pathway can be constructed and arranged to receive fluid via at least one of manual feed such as with a syringe or automatic feed such as with a pump.

In some embodiments, the patient access device further comprises a vibrating element constructed and arranged to disrupt gas bubbles. The vibrating element can be constructed and arranged to vibrate the shaft and physically disrupt air bubbles on the elongate probe.

In some embodiments, the portions of the shaft comprise a transparent compliant material constructed and arranged to allow a user to manually massage out visible gas bubbles within the lumen. The patient access device can further comprise a support element within the compliant portion of the shaft.

According to another aspect of the present invention, a patient access device comprises a proximal end, a distal end, and a lumen therethrough. The device further comprises a hollow shaft, and at least a portion of the lumen passes through the shaft. The device further comprises an input port constructed and arranged to receive an elongate probe. The device further comprises a liquid supply port in fluid communication with the lumen, and the patient access device is constructed and arranged to prevent gas from passing from the proximal end to the distal end as the elongate probe is advanced through the lumen.

According to another aspect of the present invention, a method of using a patient access device comprises inserting an elongate probe into a lumen at a proximal end of the patient access device. The method further comprises flowing fluid into the lumen through a liquid supply port in fluid communication with the lumen. The method further comprises flushing fluid over at least a portion of the elongate probe while it is positioned in the lumen to perform a function selected from the group consisting of one or more of: reduce gas from entering the lumen; drive gas toward a proximal end of the patient access device; and/or combinations and/or sub-combinations thereof.

In some embodiments, the method further comprises closing a valve assembly positioned on a distal portion of the patient access device prior to flowing the fluid into the lumen.

In some embodiments, the method further comprises coupling a patient introducer assembly to a distal end of the patient access device. The method can further comprise percutaneously inserting the patient introducer assembly into a blood vessel of a patient.

In some embodiments, the liquid supply port is positioned on a proximal portion of the patient access device.

In some embodiments, the liquid supply port is positioned on a distal portion of the patient access device.

In some embodiments, the method further comprises detecting the insertion of the elongate probe into the input port with a sensor and the fluid delivery assembly is configured to automatically deliver fluid based on one or more signals produced by the sensor.

In some embodiments, the method further comprises detecting a gas bubble in the lumen with a gas bubble detector.

According to another aspect of the present invention, a delivery device for delivering an elongate probe into a vascular introducer comprises a proximal end, a distal end and a lumen therethrough. The device further comprises a hollow shaft, and at least a portion of the lumen passes through the shaft. The device further comprises a funnel shaped input port constructed and arranged to receive a distal portion of an elongate probe. The device further comprises a liquid supply port in fluid communication with the lumen and the delivery device is configured to perform a function selected from the group consisting of one or more of: remove gas bubbles from the lumen; reduce gas bubbles from exiting the lumen; reduce gas bubbles from entering the lumen; and/or combinations and/or sub-combinations thereof.

In some embodiments, the funnel shaped input port is constructed and arranged to radially compact an expanded portion of the elongate probe.

In some embodiments, the device further comprises at least one fluid delivery tube, and the shaft comprises a distal portion and the at least one fluid delivery tube extends to said shaft distal portion. The at least one fluid delivery tube can comprise multiple delivery tubes. The at least one fluid delivery tube can comprise multiple outlet ports in fluid communication with the lumen. The at least one fluid delivery tube can be in fluid communication with the liquid supply port. The at least one fluid delivery tube can comprise an outlet port constructed and arranged such that delivered fluid travels both toward the patient access device proximal end and the patient access device distal end.

In some embodiments, the liquid supply port comprises a luer.

In some embodiments, the liquid supply port comprises a shutoff valve.

According to another aspect of the present invention, provided is a patient access device as shown in the drawings.

According to another aspect of the present invention, provided is a delivery device configured to deliver an elongate probe into a vascular introducer as shown in the drawings.

According to another aspect of the present invention, provided is a method of treating a patient using a patient access device as shown in the drawings.

According to another aspect of the present invention, provided is a method of diagnosing a patient using a patient access device as shown in the drawings.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention.

DETAILED DESCRIPTION

Figure 1A:
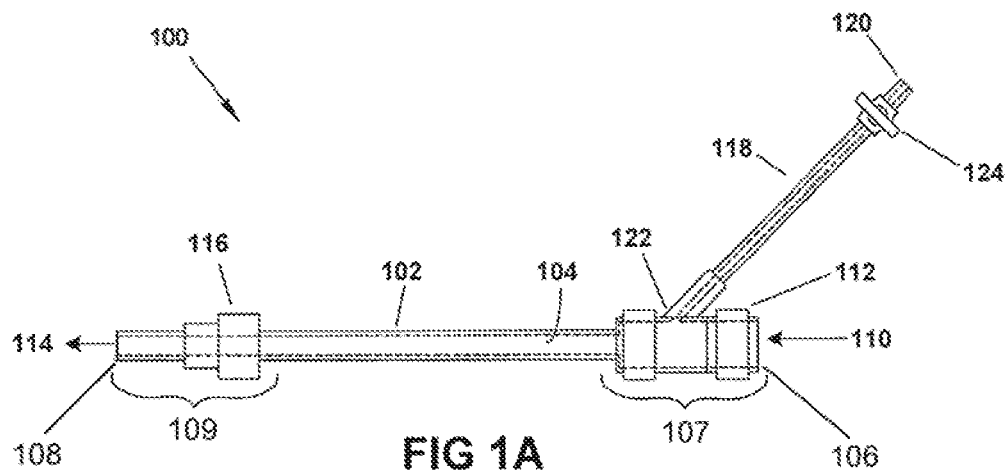
FIGS. 1A and 1B illustrate one embodiment of a patient access device constructed and arranged to prevent gas from exiting a distal end of a lumen of the device while a portion of an elongate medical device or other elongate probe is within the lumen, consistent with aspects of the present invention.

Embodiments of the invention will now be described with reference to the figures, wherein like numerals reflect like elements throughout. The present inventive concept may, however, be embodied in many different forms and should not be construed as limited to the exemplary embodiments set forth herein.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used and/or an end opposite the distal end. A distal end refers to the end of a component further from the operator and/or extending towards the surgical area of a patient and/or the implant.

For many diagnostic or therapeutic clinical procedures (e.g. percutaneous procedures), it is critical to prevent the introduction of air or other gas into the patient (e.g. into the patient's vascular system) when an elongate probe, such as a catheter or other elongate medical device, is inserted into the patient. The inserted elongate probes or other medical devices can include but are not limited to: guidewires, balloon catheters, stent delivery catheters, ablation catheters, neurovascular catheters, embolization catheters, and many other types of insertable medical devices that can be used to diagnose or treat a wide variety of diseases or disorders within the patient. In some embodiments, an inserted elongate probe can include a complex shape or non-tubular shape (e.g. on the distal end or a distal portion of the probe) that is likely to trap air or other gas when introduced, such as a catheter with an expandable array distal portion. In some embodiments, the expandable array comprises an element selected from the group consisting of one or more of: a spiral array; a basket construction array; an array of transducers; an array of sensors and/or transducers; an array of electrodes; and/or combinations and/or sub-combinations of these.

In accordance with the present invention, there are provided an improved device, system and method for preventing or at least reducing air or other gas bubbles from entering a patient body lumen (e.g. a vein or artery of the patient's cardiovascular system) during a percutaneous procedure by using a patient access device constructed and arranged to prevent or at least reduce gas from exiting a distal end of the patient access device, such as during advancement of an elongate medical device or other elongate probe (e.g. a catheter or other percutaneous device) into the patient's body lumen. In some embodiments, the patient access device is constructed and arranged to evacuate air or other gas bubbles from the patient access device.

Figure 1B:
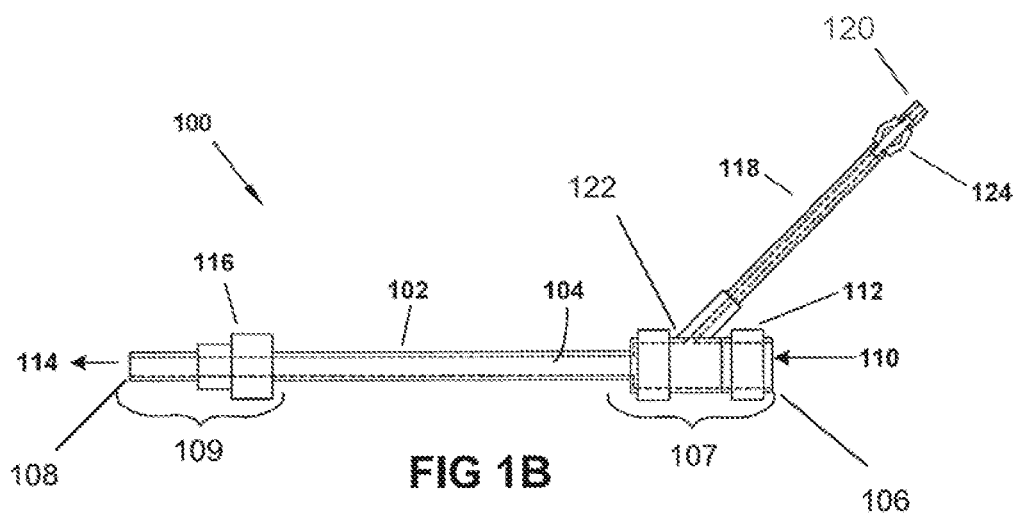

FIGS. 1A and 1B show one embodiment of a patient access device 100 having a hollow shaft 102, a proximal end 106, a proximal portion 107, a distal end 108, a distal portion 109, and a lumen 104 extending from proximal end 106 to distal end 108. In some embodiments, shaft 102 passes fully through proximal portion 107 and distal portion 109 such that shaft 102 comprises lumen 104. In other embodiments, shaft 102 terminates at or within a portion of portions 107 and/or 109, such that lumen 104 extends beyond shaft 102 on either or both ends of shaft 102. In some embodiments, patient access device 100 is constructed and arranged to attach to or be inserted into a vascular introducer. In other embodiments, distal portion 109 comprises or forms a conduit (e.g. a distal portion of shaft 102), through which lumen 104 fluidly continues, that is constructed and arranged to be percutaneously inserted into the patient's vascular system, avoiding the need for a separate vascular introducer. Proximal portion 107 includes an input port 110 and a valve assembly 112 configured to restrict fluid flow between lumen 104 and an inserted elongate probe, such as a catheter (see FIG. 3B). Distal portion 109 includes an output port 114 for the elongate probe to exit toward a patient's body lumen and a valve assembly 116 configured to restrict fluid flow between lumen 104 and an introducer (e.g. a vascular introducer) and/or the patient's body lumen. In some embodiments, proximal and distal valve assemblies 112, 116 can be the same, in other embodiments, they can be different, such as when one valve assembly is configured as a higher pressure valve than the other. For example, proximal valve assembly 112 can be configured to allow a flow at a first pressure and distal valve assembly 116 can be configured to allow flow at a second, different pressure. The second pressure can be higher than the first (i.e. distal valve assembly 116 allows flow at a higher pressure than proximal valve assembly 112), or the first pressure can be higher than the second (i.e. distal valve assembly 116 allows flow at a lower pressure than proximal valve assembly 112).

Patient access device 100 further includes a liquid supply port in fluid communication with lumen 104. The liquid supply port can include a luer connector. In the embodiment shown in FIGS. 1A and 1B, the liquid supply port includes liquid supply shaft 118 with a lumen having a proximal port 120 and a distal port 122. The liquid supply shaft 118 can be a flexible tube. The proximal port 120 is configured to couple to and receive fluid from a fluid source, and the distal port 122 is in fluid communication with lumen 104. Proximal port 120 can include a luer connector fluidly attached to the fluid source. Liquid supply shaft 118 further includes a control 124 to initiate or regulate the fluid flow from the fluid source to lumen 104. Control 124 can include: a stopcock, a roller valve, a button, or other suitable valve. Control 124 can be manually operated (e.g. operator initiated), or electronically operated (e.g. automatically or electronically initiated, see also FIG. 4), or some combination thereof. Control 124 can perform multiple functions, such as initiate flow of fluid; increase or decrease rate of flow of fluid; set the volume of the flow of fluid; and combinations of these. In FIG. 1A control 124 comprises a valve in the closed position and in FIG. 1B the valve is in the open position.

Figure 1C:
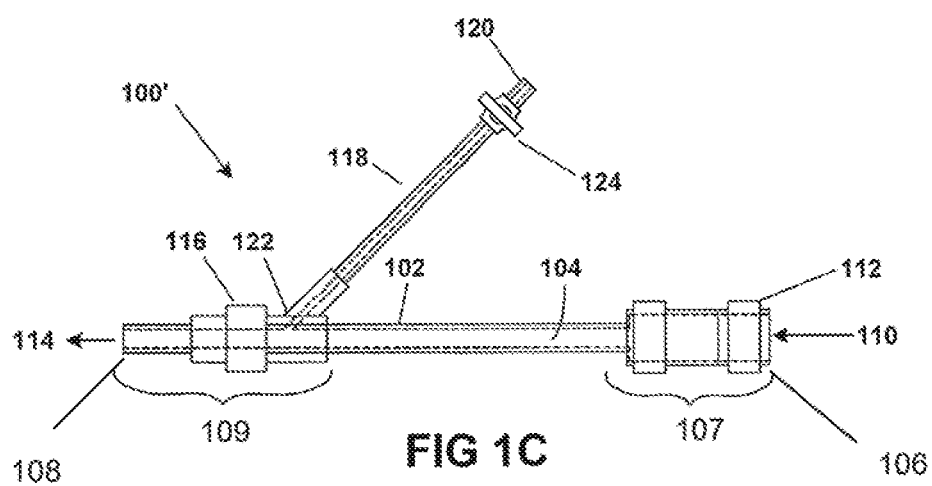
FIG. 1C illustrates another embodiment of a patient access device constructed and arranged to prevent gas from exiting a distal end of a lumen of the device while a portion of an elongate probe is within the lumen, consistent with aspects of the present invention.

Distal port 122 of liquid supply shaft 118 can be coupled at any point along lumen 104 between the proximal and distal ends 106, 108. In the embodiment shown in FIGS. 1A and 1B, the liquid supply shaft 118 is at the proximal portion 107, close to the valve assembly 112. In another embodiment shown in FIG. 1C, the patient access device 100' can include the liquid supply shaft 118 near distal portion 109 and valve assembly 116.

The patient access device 100, 100' is constructed and arranged to prevent air or other gas within lumen 104 from exiting distal end 108 while a portion of an elongate medical device or other elongate probe is advanced or otherwise disposed within lumen 104, so that gas does not enter into the patient's vascular system or other body lumen. Air or other gas can inadvertently enter the vasculature for a number of reasons. In some instances, gas from the external environment (e.g. air in a clinical procedure room environment) is drawn into a vascular introducer while a probe is advanced through the introducer. During advancement of the probe, a pressure differential can be created due to the elongate probe acting as a fully or partially sealing plug, similar to a piston in a cylinder, reducing pressure within the lumen of the introducer as the probe is inserted and "pulling" air through the room-exposed, proximal end of the introducer. Alternatively, gas can pass from the external environment through a valved proximal portion of an introducer when the valve is deformed or otherwise damaged, such as damage caused during the passage of multiple elongate probes into and out of the valve, such as when multiple probes are used in a single clinical procedure. Air or other gas bubbles can also enter an introducer lumen as they cling to an inserted probe, such as gas bubbles that become attached due to surface tension and/or the device geometry or shape. The trapped gas bubbles can enter the vasculature along with the inserted probe if not removed by the patient access device.

Patient access device 100 can be constructed of an individual biocompatible material or a combination or subcombination of two or more biocompatible materials selected from the group consisting of: metal, such as stainless steel, cobalt alloys, Ni—Ti alloys or titanium alloys; ceramic; plastic; polymers, such as polyethylene, polyvinylchloride, polyurethane or polylactide; flexible materials, such as silicone or latex; and/or combinations and/or subcombinations of these.

In some embodiments, shaft 102 can include a rigid or semi-rigid transparent material. In other embodiments, one or more portions of shaft 102 can comprise a transparent compliant material, such that the user can manually compress shaft 102 to propel any gas bubbles (e.g. visible gas bubbles) within shaft 102, such as to exit proximal portion 107. This compliant material could be supported by a support element such as a Nitinol coil, or columns, which would provide scaffolding radial support, but still allow for manual manipulation of the medical device or probe within the shaft 102.

Figure 2A:
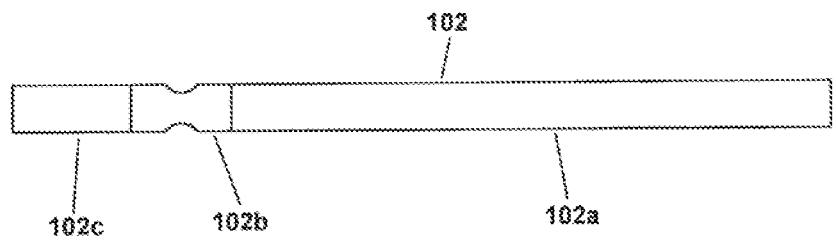
FIGS. 2A-2C illustrate one embodiment of a shaft used in the patient access device of FIGS. 1A-1C having both a rigid portion and flexible portion for forming a valve, consistent with the present invention.
Figure 2B:
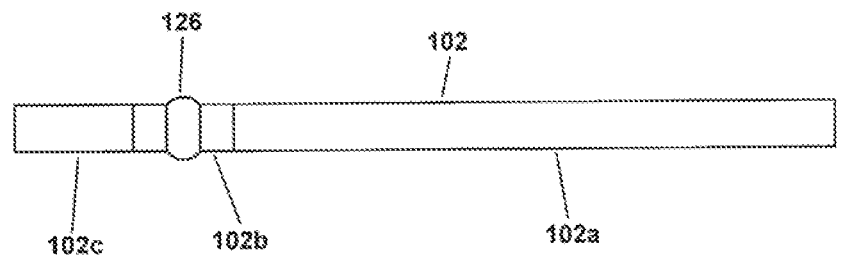
Figure 2C:
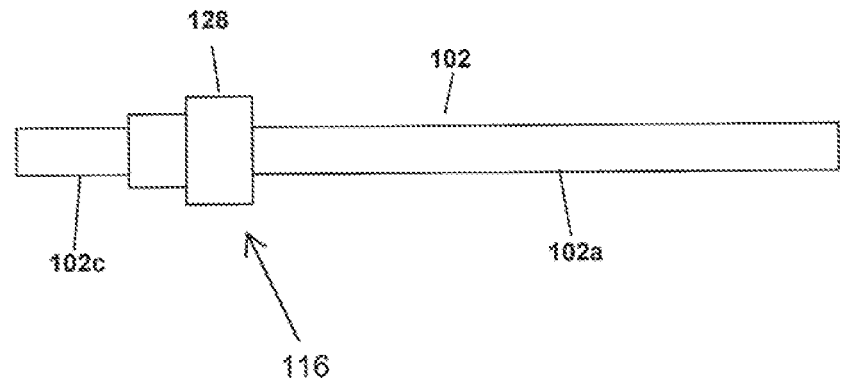

FIGS. 2A-2C illustrate one embodiment of shaft 102 comprising multiple sections, a proximal portion 102a, a compression portion 102b and a distal portion 102c. Shaft 102 can be any length so that it can be used with medical devices or probes of differing lengths. In some embodiments, shaft 102 can have a length between about 1 and about 6 inches, as an example. Proximal portion 102a and distal portion 102c can be made of a transparent tube of semi-rigid to rigid material. The compression portion 102b can be made of a low durometer tube capable of compression at low force. The compression portion 102b can be used with other pieces to make distal valve assembly 116 of FIGS. 1A-1C. FIG. 2B shows an O-ring 126 placed on compression portion 102b, for example, in a saddle or indented section of compression portion 102b. Other components, such as a compressible collar 128, can be added, shown in FIG. 2C over the compression portion 102b and the O-ring 126 to create a valve, distal valve assembly 116 as shown, for example, a Tuohy Borst valve. While this embodiment shows only one compression portion 102b shown on the shaft 102, it is understood that more than one compression portion 102b can be positioned along shaft 102 forming multiple valves, for example, this arrangement can also be used to form the proximal valve 112 of FIGS. 1A-1C.

FIGS. 3A-3D illustrate one embodiment of the patient access device 100 with an elongate medical device or other elongate probe having a functional segment 146 and a shaft portion 148. Various methods of using the elongate medical device or other elongate probe with the patient access device 100, e.g., diagnostic or therapeutic methods, may be readily understood by those skilled in the art based on this disclosure.

Figure 3A:
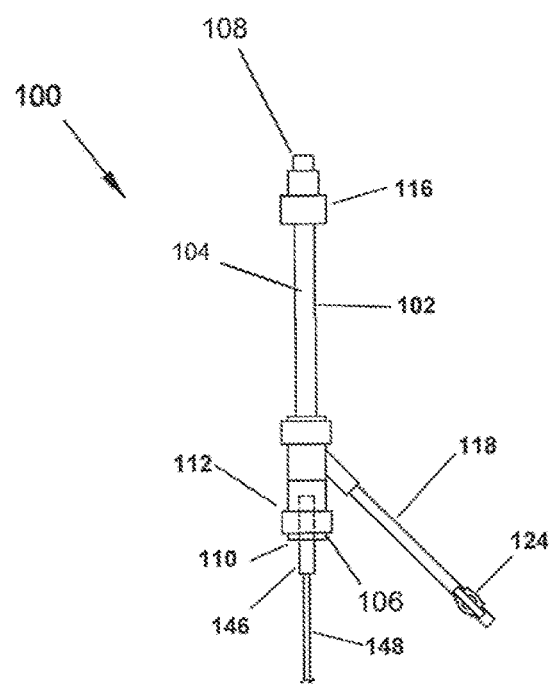
FIG. 3A-3D illustrates one embodiment of the patient access device of FIGS. 1A-1C with an elongate probe, consistent with aspects of the present invention.
Figure 3B:
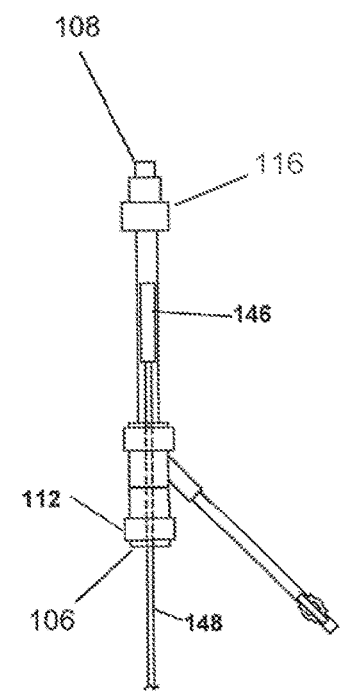
Figure 3C:
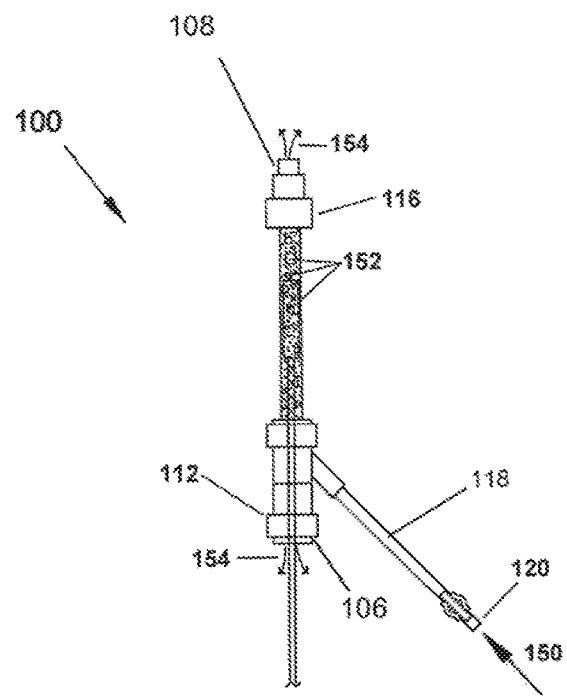
Figure 3D:
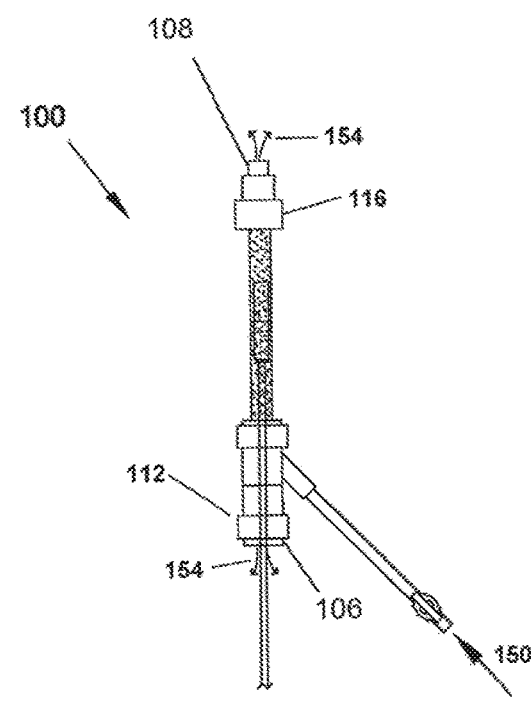

In some embodiments, functional segment 146 can comprise an expandable element, such as an array of sensors or transducers mounted to an expandable basket or other structure that may tend toward capturing air bubbles during insertion. Functional segment 146 can be constructed and arranged to perform a diagnostic or therapeutic event or function in a clinical procedure. In some embodiments, the diagnostic event or function comprises recording electrical signals or ultrasound signals, such as when functional segment 146 comprises an array of sensors positioned in a chamber of a heart. In some embodiments, the therapeutic event or function comprises delivering energy to cardiac tissue, such as when functional segment 146 comprises an array of electrodes configured to deliver radiofrequency energy to tissue. Functional segment 146 is inserted into input port 110 at proximal end 106, with valve assembly 112 in the open position (FIG. 3A). Functional segment 146 is then positioned within lumen 104. Valve assembly 112 is then closed around shaft portion 148 and sealed (FIG. 3B). At this point, all that is in lumen 104 is functional segment 146, some of the shaft portion 148 and potentially one or more air or other gas bubbles. Water or fluid 150, for example sterile saline, is then introduced into lumen 104 via liquid supply shaft 118. For example, fluid 150 can be in a syringe, IV bag or fluid pump coupled to proximal port 120. As fluid 150 continues to fill lumen 104, gas bubbles 152 can form (FIG. 3C). In one embodiment, to remove the bubbles 152, the proximal valve 112 and/or the distal valve 116 can be slightly opened to allow some of fluid 150 to seep out 154. In another embodiment, to remove the bubbles 150, one valve assembly can be configured at a higher pressure than the other valve, and the lower pressure valve assembly can allow some of the fluid 150 to seep out 154, while the higher pressure valve assembly does not. By having transparent sides on shaft 102, this procedure can be viewed and manually continued until the bubbles 152 are gone (FIG. 3D).

If the patient access device 100 is being used during a percutaneous procedure and the elongate medical device or other elongate probe needs to be changed, the steps described hereabove can be modified. In this embodiment, the patient access device 100 is constructed and arranged to prevent air or other gas bubbles from passing from the distal end 108 and into the patient's body lumen, as the elongate probe is advanced through lumen 104. For example, when the first probe is in use, distal valve 116 will be attached or be part of an introducer (e.g. a vascular introducer). For an exchange of elongate probes, the first probe is pulled back into lumen 104 and distal valve 116 is closed, to prevent blood from entering lumen 104 and/or to prevent gas bubbles from lumen 104 entering the patient's body lumen. The first probe is then removed through proximal valve 112. The second probe is then inserted into lumen 104. Since it is in use, there can already be some fluids, such as blood, within lumen 104 along with one or more gas bubbles. Once functional segment 146 and some of shaft portion 148 are inside lumen 104, valve assembly 112 is then closed around shaft portion 148 and sealed. Fluid 150 is then introduced into lumen 104 via liquid supply shaft 118 (like in FIG. 3C). To remove any gas bubbles 152, proximal valve 112 can be slightly opened to allow some of fluid 150 and blood to seep out 154. By having transparent sides on shaft 102, this procedure can be viewed and manually continued until bubbles 152 are gone. Once the gas bubbles are gone, distal valve 116 can be opened and functional segment 146 can continue advancement, through the introducer and into the patient's body lumen. In some embodiments, distal valve assembly 116 can be a valve assembly constructed and arranged at a sufficiently high pressure to prevent fluid leakage or seepage during use, and the proximal valve assembly 112 can be a valve assembly constructed and arranged at a sufficiently low pressure to allow fluid leakage or seepage during use.

Figure 4:
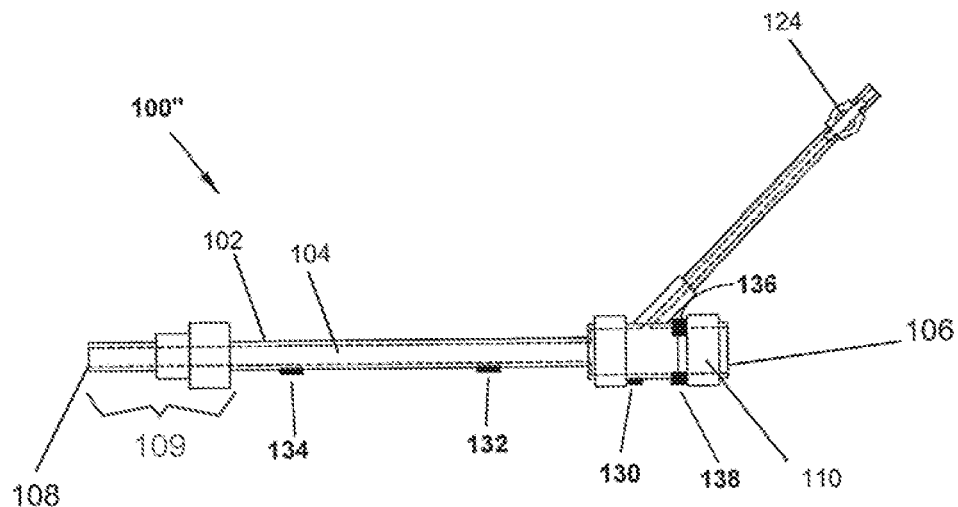
FIG. 4 illustrates one embodiment of a "smart" patient access device having additional components to increase the patient access device capability, consistent with aspects of the present invention.

FIG. 4 shows one embodiment of a "smart" patient access device 100″, similar to patient access device 100, but including additional components to increase its capability. For example, patient access device 100″ can include one or more of the following: a detection sensor 130, a flow sensor 132, a bubble detector 134, a battery 136 and an alarm transducer 138. These additional components can allow for more automation of the insertion or exchange procedures of the probe into the patient's body lumen. Additionally, the additional components can increase the safety aspects of the patient access device. In some embodiments, the detection sensor 130 can be used to detect insertion of a probe's functional segment 146 into input port 110 and/or lumen 104. The detection sensor 130 can also be connected to an electronically operated control 124 on the fluid delivery system to automatically deliver fluid based on one or more signals produced by sensor 130, such as detection of an elongate probe inserted into input port 110 and/or lumen 104. In some embodiments, flow sensor 132 is designed to produce a signal based on the fluid flow through lumen 104. The signal can be used to maintain fluid flow above a certain flow rate, for example, above 1 ml/min. In some embodiments, flow sensor 132 is configured to produce a signal corresponding to the flow rate or volume of fluid flowing through the lumen 104. In some embodiments, bubble detector 134 is configured to detect gas bubbles in lumen 104. Bubble detector 134 can be placed at any desired location lumen 104, for example, in and/or proximate to distal portion 109, or in and/or proximate to shaft 102. In some embodiments, bubble detector 134 can be an ultrasound bubble detector. The components can require power, so in some embodiments a power supply can be provided, such as battery 136. In some embodiments, alarm transducer 138 can be used, for example, an audio or tactile transducer, to activate an alarm when one or more conditions are detected. The alarm conditions that can be detected include, but are not limited to, one or more of the following: absence of flow; flow rate below a threshold; presence of a gas bubble; advancement of elongate probe; and combinations of these.

Figure 5:
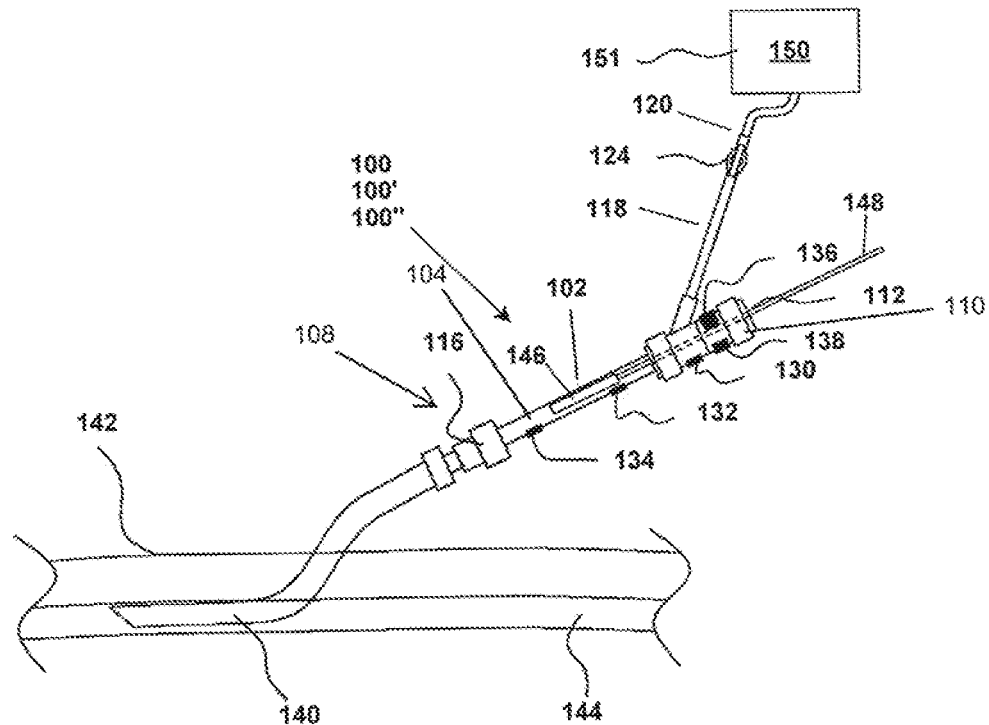
FIG. 5 illustrates the use of the patient access device of FIGS. 1A, 1C or 4, consistent with aspects of the present invention.

FIG. 5 shows the patient access device 100, 100′ or 100″ (generally 100) in use with an elongate medical device or other elongate probe for a percutaneous procedure. In the embodiment shown, an introducer 140 has been inserted through the patient's skin 142 accessing the patient's body lumen 144. The distal end of introducer 140 is positioned within the patient's body lumen 144 while the proximal end is coupled to distal end 108 of the patient access device. In some embodiments, the introducer 140 is a separate component, while in other embodiments, the introducer 140 is an extension or part of the distal end 108 of patient access device 100. Patient access device 100 is constructed and arranged to prevent gas bubbles from passing from the distal end 108 into a patient's body lumen 144 as an elongate probe is advanced through lumen 104. Functional segment 146 is inserted into input port 110 and positioned within lumen 104. Valve assembly 112 is then closed around shaft portion 148 and sealed. Water or fluid 150, for example sterile saline, from a fluid delivery system 151 is then introduced into lumen 104 via liquid supply shaft 118 having control 124. For example, fluid delivery system 151 can be a syringe, IV bag or fluid pump, such as a peristaltic pump or other suitable pump. As fluid 150 continues to fill lumen 104, gas bubbles 152 can form (see FIG. 3C). In one embodiment, to remove bubbles 152, proximal valve assembly 112 can be slightly opened to allow some of fluid 150 to seep out 154 (see FIG. 3C). In another embodiment, distal valve assembly 116 can be a higher pressure valve than proximal valve assembly 112, such that proximal valve assembly 112 allows some of the fluid 150 to seep out 154 to remove bubbles 150, while the higher pressure distal valve assembly 116 does not allow fluid to pass. By having transparent sides on shaft 102, this procedure can be viewed and manually continued until bubbles 152 are gone. Once bubbles 152 are viewed to be removed, distal valve assembly 116 can be opened and functional segment 146 can be inserted through introducer 140 and into the patient's body lumen 144, such as for subsequent diagnosis and/or treatment.

If the patient access device is the "smart" patient access device 100" additional steps can be performed. For example, detection sensor 130 can detect insertion of a probe's functional segment 146 into input port 110 and/or within lumen 104, such as to then send signals to the electronically operated control 124 on the fluid delivery system to automatically deliver fluid to the lumen 104 of the shaft 102. Flow sensor 132 can produce a signal based on the fluid flow through lumen 104. The signal can include detection of the rate of fluid flow through lumen 104. Bubble detector 134 can be used to detect one or more gas bubbles in lumen 104. The components can be powered by battery 136. Alarm transducer 138 can emit an alarm when one or more conditions are detected, such as: absence of flow; flow rate below a threshold; presence of a gas bubble; advancement of elongate probe; and combinations of these.

Sometimes, the elongate medical device or other elongate probe can need to be exchanged during a procedure for another probe. For an exchange, the first probe can be pulled back from the patient's body lumen 144 through the introducer 140 and into lumen 104. The distal valve 116 can then be closed to prevent blood from entering lumen 104 and/or prevent gas bubbles from lumen 104 entering the patient's body lumen 144. The first probe can then be removed through proximal valve 112. The second probe can then be inserted into lumen 104 and proximal valve 112 can be closed. Since it is in use, there can already be some fluids, such as blood, within lumen 104 along with one or more gas bubbles. Once functional segment 146 and some of shaft portion 148 of the second probe is inside lumen 104, valve assembly 112 can then be closed around shaft portion 148 and sealed, and fluid 150 can then be introduced into lumen 104 via liquid supply shaft 118. At this point, the rest of the procedure is the same as described hereabove to remove bubbles 152 and once bubbles are absent, distal valve assembly 116 can be opened and functional segment 146 of the second probe can be inserted through introducer 140 and into the patient's body lumen 144, such as for subsequent diagnosis and/or treatment.

Figure 6A:
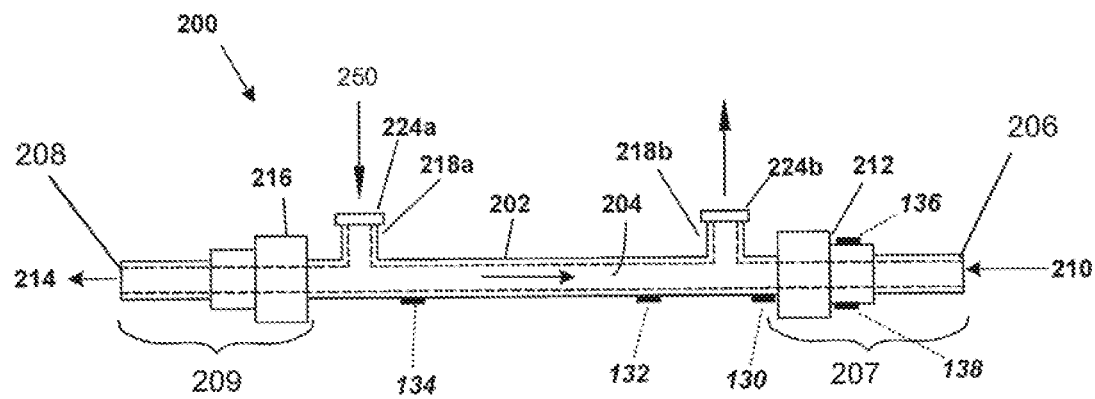
FIG. 6A illustrates another embodiment of a patient access device having both input and output liquid supply ports in an "open" fluid system that does not recirculate the fluid during use, in accordance with aspects of the present invention.
Figure 6B:
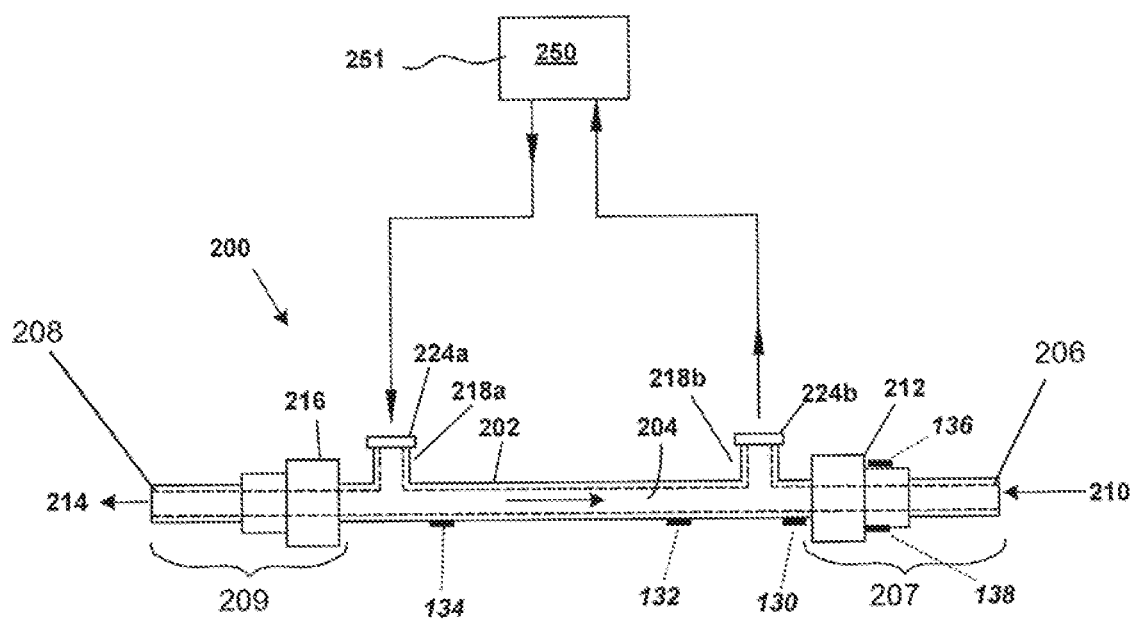
FIG. 6B illustrates another embodiment of a patient access device having both input and output liquid supply ports in a "closed" fluid system that is configured to recirculate the fluid during use, in accordance with aspects of the present invention.

FIGS. 6A and 6B show other embodiments of a patient access device 200 having a hollow shaft 202, a proximal end 206, a proximal portion 207, a distal portion 209, a distal end 208, and a lumen 204 extending from proximal end 206 to distal end 208. The proximal portion 207 includes an input port 210 and valve assembly 212 configured to restrict flow between lumen 204 and an inserted elongate probe, such as a catheter or other percutaneous device. Distal portion 209 includes an output port 214 for the elongate probe to exit toward a patient's body lumen and valve assembly 216 configured to restrict fluid flow between lumen 204 and patient's body lumen. In some embodiments, the proximal and distal valve assemblies 212, 216 can be the same, in other embodiments, they can be different, such as one valve assembly can constructed and arranged to operate at a higher pressure than the other valve assembly. For example, proximal valve assembly 212 can allow a flow at a first pressure and the distal valve assembly 216 can allow flow at a second, different pressure. The second pressure can be higher than the first (i.e. distal valve assembly 216 allows flow at a higher pressure than proximal valve assembly 212), or the first pressure can be higher than the second (i.e. distal valve assembly 216 allows flow at a lower pressure than proximal valve assembly 212).

Patient access device 200 further includes a liquid supply input port 218a and a liquid supply output port 218b in fluid communication with lumen 204. The liquid supply input and output ports, 218a and 218b can include luer connectors. The liquid supply input port 218a is configured to couple and receive fluid from a fluid source and deliver fluid to lumen 204. The liquid supply output port 218b is configured to allow fluid to exit from lumen 204. The liquid supply output port 218b can also include a check valve or one way valve 224b that allows fluid to only flow out of lumen 204 and does not let air or other gas into lumen 204. The liquid supply input port 218a can further include a control 224a, such as described hereabove for control 124, to initiate or regulate the fluid flow from the fluid source to lumen 204. Control 224a can include a stopcock, a roller valve or a button. Control 224a can be manually operated (e.g. operator initiated), or electronically operated (e.g. automatically start the fluid flow). Control 224a can perform multiple functions, such as initiate flow of fluid; increase or decrease rate of flow of fluid; set the volume of the flow of fluid; and combinations thereof. The patient access device 200 can also include "smart" patient access device features, such as described hereabove for "smart" patient access device 100", having one or more of the following: a detection sensor 130, a flow sensor 132, a bubble detector 134, a battery 136 and an alarm transducer 138.

FIG. 6A shows a patient access device 200 that comprises an "open" fluid system that does not recirculate fluid 250 during use. A fluid source, such as a syringe, IV bag or fluid pump, is coupled to liquid supply input port 218a. Fluid 250 enters liquid supply input port 218a via control means 224a, flows through lumen 204 and exits liquid supply output port 218b through check valve or one way valve 224b.

FIG. 6B shows a patient access device 200 that comprises a "closed" fluid system that is configured to recirculate fluid 250 during use. Fluid 250 is stored in a recirculating fluid delivery system 251 that includes a fluid pumping means. Recirculating fluid delivery system 251 is coupled to both liquid supply input port 218a and liquid supply output port 218b. Fluid 250 enters the liquid supply input port 218a via control means 224a, flows through lumen 204 and exits liquid supply output port 218b through one way valve 224b and returns to recirculating fluid delivery system 251.

Within recirculating fluid delivery system 251, gas bubbles are extracted or percolate from the fluid 250 and then the fluid is used again.

Figure 7:
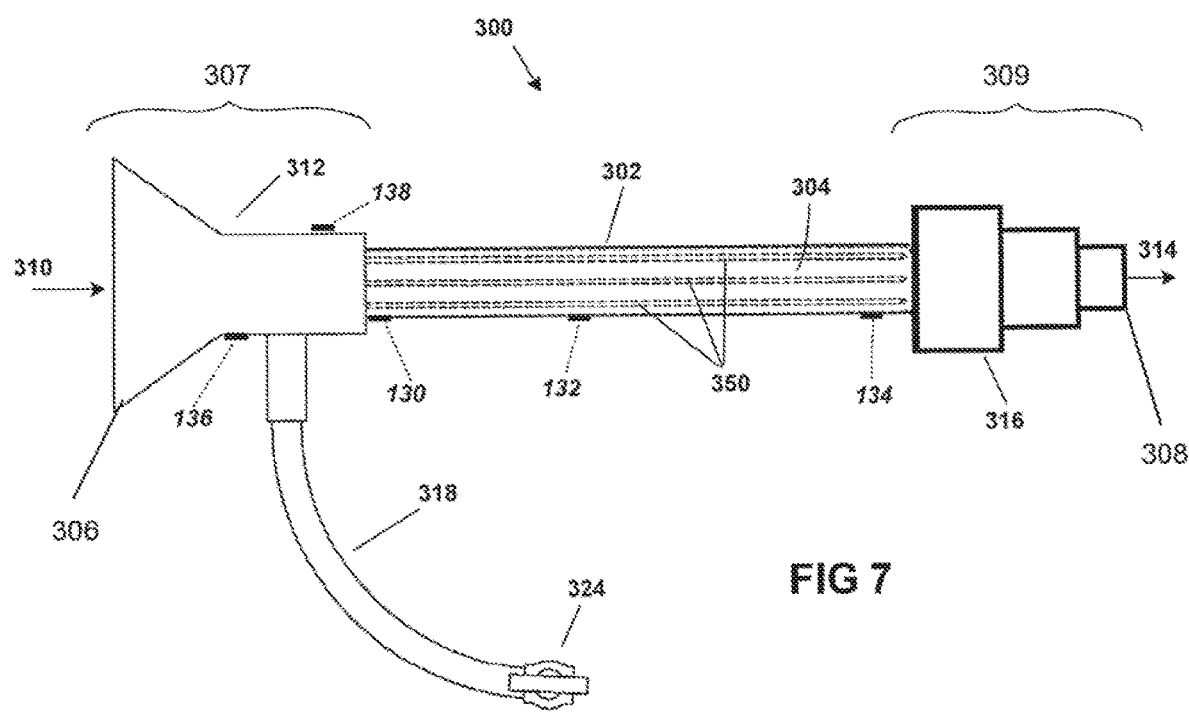
FIG. 7 illustrates another embodiment of a patient access device having an input port with funnel shaped assembly and least one fluid delivery tube within a lumen of the patient access device, consistent with aspects of the present invention.
Figure 8A:
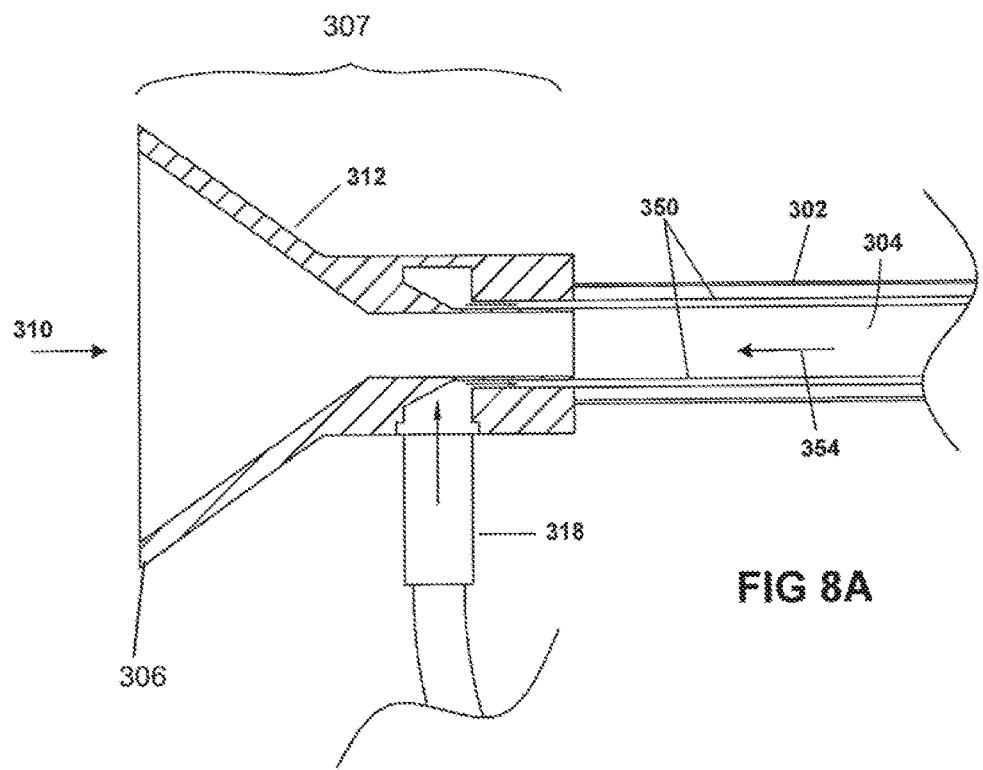
FIGS. 8A and 8B illustrate sectional views of the proximal and distal ends of the patient access device of FIG. 7, consistent with aspects of the present invention.
Figure 8B:
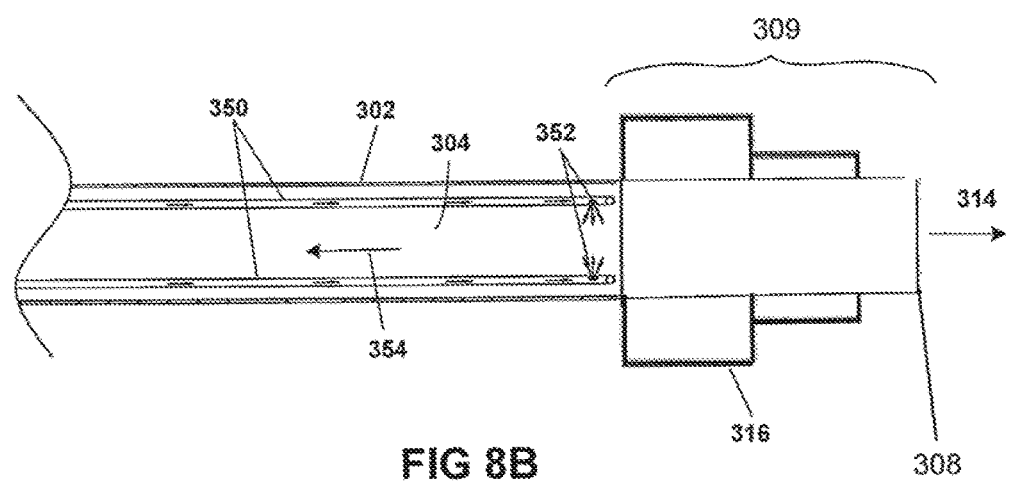

FIGS. 7, 8A and 8B show another embodiment of a patient access device 300 having a shaft 302, a proximal end 306, a proximal portion 307, a distal portion 309, a distal end 308, and a lumen 304 extending from proximal end 306 to distal end 308. The proximal portion 307 includes an input port 310 and funnel shaped assembly 312 configured to receive a distal portion of an elongate probe, such as a catheter or other percutaneous device. Funnel shaped assembly 312 can also be configured to radially compact an expanded portion of the elongate probe during insertion. Distal portion 309 includes an output port 314 for the elongate probe to exit toward a patient's body lumen and valve assembly 316 configured to restrict fluid flow 354 (see FIGS. 8A and 8B) between lumen 304 and the patient's body lumen. Shaft 302 includes at least one fluid delivery tube 350. Fluid delivery tubes 350 can be within the wall of shaft 302 and/or positioned within lumen 304, for example, proximal lumen 304 wall of shaft 302. Fluid delivery tubes 350 can extend along shaft 302 for any length desired, for example, fluid delivery tubes 350 can extend from the proximal portion 307 to distal portion 309. In some embodiments, there are multiple fluid delivery tubes 350. Each of the fluid delivery tubes 350 includes at least one outlet port 352 in fluid communication with lumen 304. In the embodiment shown, fluid delivery tubes 350 are coupled with funnel shaped assembly 312 (see FIG. 8A).

Patient access device 300 further includes a liquid supply port 318 in fluid communication with lumen 304 via fluid delivery tubes 350 and outlet ports 352. In the embodiment shown, shaft 302 liquid supply port 318 is coupled with funnel shaped assembly 312 (see FIG. 8A). Liquid supply input port 318 is configured to couple and receive fluid from a fluid source and deliver fluid to lumen 304 via fluid delivery tubes 350 and outlet ports 352. Liquid supply input port 318 can further include a control 324, such as is described hereabove for control 124, to initiate or regulate the fluid flow 354 from the fluid source to lumen 304. Control 324 can include a stopcock, a roller valve or a button. Control 324 can be manually operated (e.g. operator initiated), or electronically operated (e.g. automatically start the fluid flow 354). Control 324 can perform multiple functions, such as: initiate flow of fluid; increase or decrease rate of flow of fluid; set the volume of the flow of fluid; and combinations thereof. Patient access device 300 can also include "smart" patient access device features, such as described hereabove for "smart" patient access device 100", having one or more of the following: a detection sensor 130, a flow sensor 132, a bubble detector 134, a battery 136 and an alarm transducer 138.

Figure 9A:
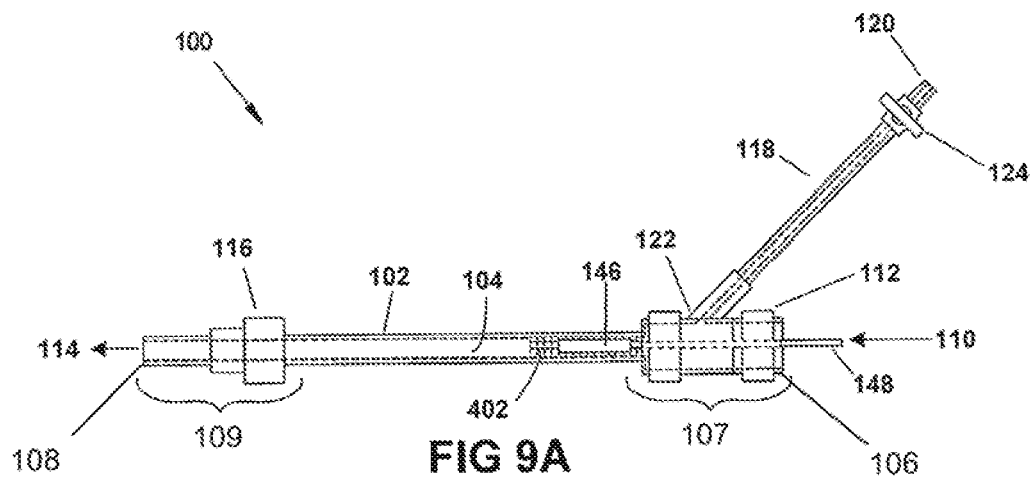
FIG. 9A illustrates another embodiment of the patient access device of FIGS. 1A-1C constructed with a wiper or brush within a lumen of the patient access device to assist in preventing gas from exiting the distal end of the lumen while a portion of an elongate probe is within the lumen, consistent with aspects of the present invention.
Figure 9B:
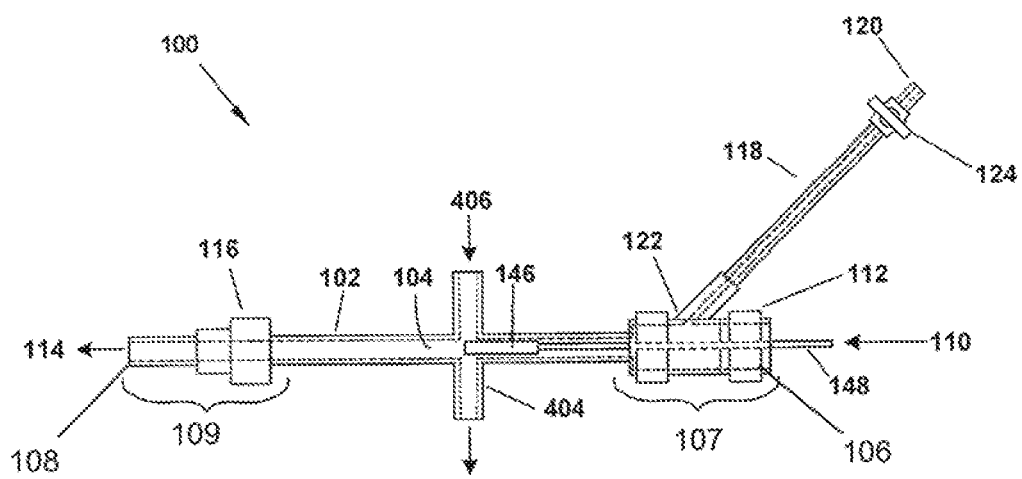
FIG. 9B illustrates another embodiment of the patient access device of FIGS. 1A-1C constructed with a second fluid pathway intersecting the lumen which allows for a second current of water, or "water curtain" to be flushed over the probe to assist in preventing gas from exiting the distal end of the lumen while a portion of the probe is within the lumen, consistent with aspects of the present invention.
Figure 9C:
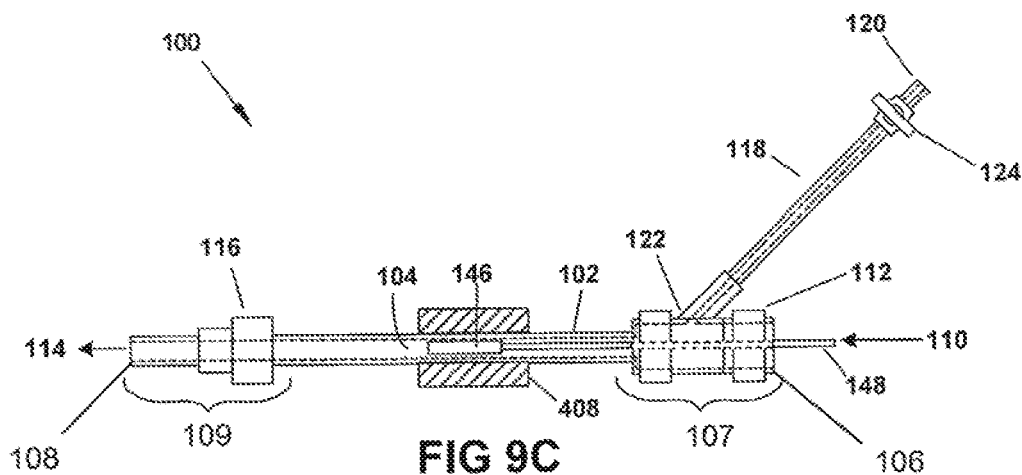
FIG. 9C illustrates another embodiment of the patient access device of FIGS. 1A-1C constructed with an ultrasonic or other mechanical vibrator attached or coupled to the patient access device to assist in preventing gas from exiting the distal end of the lumen while a portion of an elongate probe is within the lumen, consistent with aspects of the present invention.

FIGS. 9A-9C show additional features that can be added to any of the patient access devices discussed above. While these features are shown with regard to patient access device 100, they also can be part of patient access device 100', 100", 200 or 300. FIG. 9A shows an embodiment of the patient access device having a gas disrupting component 402, such as a wiper or brush, positioned within lumen 104 and constructed and arranged to disrupt gas bubbles as the elongate medical device or other elongate probe functional segment 146 is inserted through shaft 102. Gas disrupting component 402 can comprise small fibers or other material to brush and disrupt air bubbles as the probe passes gas disrupting component 402. FIG. 9B shows an embodiment having a second fluid pathway 404 intersecting lumen 104 which allows for a second current of water, or "water curtain" 406 to be flushed over functional segment 146 as it passes, similar to the air blow dryers at a car wash. The second fluid pathway can be manually fed with fluid, such as with a syringe, or automatically fed with fluid via a pump or other means (not shown). The fluid in the second fluid can be the same or can be a different fluid than the first fluid flowing through the shaft lumen. FIG. 9C shows one embodiment of a vibrating element 408, such as an ultrasonic or other mechanical vibrator, attached or coupled to the shaft 102. Vibrating element 408 is configured to vibrate shaft 102 and physically disrupt gas bubbles within lumen 104 and/or on functional segment 146.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

We claim:

1. A patient access device, comprising:
   an elongate hollow shaft comprising a proximal end, a distal end, and a lumen therethrough;
   an input port coupled to the proximal end configured to receive an elongated probe, the input port comprising a first valve assembly configured to allow fluid flow;
   an output port coupled to the distal end and configured to receive the elongated probe, the output port comprising a second valve assembly configured to allow fluid flow;
   a liquid supply port between the input port and the output port and in fluid communication with the lumen, the liquid supply port configured to deliver fluid to the lumen; and
   a gas disrupting component positioned within the lumen;
   wherein the patient access device is configured to flush fluid over at least a portion of the elongated probe positioned in the lumen, and
   wherein the gas disrupting component is configured to disrupt bubbles as the elongated probe passes the gas disrupting component.

2. The device of claim 1, wherein the gas disrupting device comprises a wiper.

3. The device of claim 1, wherein the gas disrupting device comprises a brush.

4. The device of claim 1, wherein the gas disrupting device comprises small fibers.

5. The device of claim 1, wherein the gas disrupting device comprises a vibrating element.

6. The device of claim 1, further comprising a fluid delivery assembly connected to the input port and configured to deliver fluid to the lumen of the shaft.

7. The device of claim 6, wherein the fluid delivery assembly includes a sensor configured to detect insertion of the elongated probe into the input port and the fluid delivery assembly is further configured to automatically deliver fluid based on one or more signals produced by the sensor.

8. The device of claim 6, wherein the fluid delivery assembly includes one or more controls configured to allow an operator to perform a function selected from the group consisting of: initiate flow of fluid; increase or decrease rate of flow of fluid; set the magnitude of the flow of fluid; and/or combinations thereof.

9. The device of claim 1, wherein a portion of the shaft is transparent and is made of a compliant material having a support element configured to enable a user to manually massage out any visible air bubbles within the shaft.

10. The device of claim 1, wherein the patient access device is constructed of one or more biocompatible materials selected from the group consisting of: metal; stainless steel; a cobalt alloy; a nickel titanium alloy, a titanium alloy; ceramic; plastic; a polymer; polyethylene; polyvinylchloride; polyurethane; a polylactide; silicone; latex; and/or combinations thereof.

11. The device of claim 1, further comprising one or more sensors configured to detect insertion of the elongated probe into the input port and/or the hollow shaft.

12. The device of claim 1, further comprising one or more sensors including a flow sensor configured to detect a fluid flow through the lumen.

13. The device of claim 1, further comprising one or more sensors including a gas bubble detector configured to detect a gas bubble in the lumen of the shaft.

14. The device of claim 1, further comprising an alarm transducer configured to activate an alarm when a condition is detected, wherein said condition is selected from the group consisting of: absence of flow; flow rate below a threshold; presence of a gas bubble; advancement of elongated probe; and/or combinations thereof.

15. The device of claim 1, wherein the elongated probe is selected from the group consisting of: guidewires; balloon catheters; stent delivery catheters; ablation catheters; neurovascular catheters; embolization catheters; and/or other insertable medical devices used to diagnose or treat a wide variety of diseases or disorders.

16. The device of claim 1, wherein the elongated probe comprises an expandable array selected from the group consisting of: a spiral array; a basket construction array; an array of transducers; an array of sensors and/or transducers; an array of electrodes; and/or combinations and/or sub-combinations of these.

17. The device of claim 1, wherein the first valve assembly and/or the second valve assembly comprises a Tuohy-borst valve assembly.

18. The device of claim 1, wherein the liquid supply port comprises a first fluid port and the patient access device further comprises a second fluid port.

19. The device of claim 18, wherein the second fluid port comprises a second liquid supply port.

20. The device of claim 18, wherein the second fluid port comprises a fluid output port.

* * * * *